US012115120B2

(12) United States Patent
Pritchard et al.

(10) Patent No.: US 12,115,120 B2
(45) Date of Patent: Oct. 15, 2024

(54) DIAGNOSTIC AND THERAPEUTIC SPLINTS AND METHODS OF USE

(71) Applicant: The Florida State University Research Foundation, Inc., Tallahassee, FL (US)

(72) Inventors: Emily Pritchard, Tallahassee, FL (US); Mina-Michael Barsoum, Tallahassee, FL (US); Judy Delp, Tallahassee, FL (US); Joshua Maraj, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 540 days.

(21) Appl. No.: 17/234,346

(22) Filed: Apr. 19, 2021

(65) Prior Publication Data

US 2021/0322249 A1   Oct. 21, 2021

Related U.S. Application Data

(60) Provisional application No. 63/011,587, filed on Apr. 17, 2020.

(51) Int. Cl.
*A61H 1/02* (2006.01)
*A61B 5/00* (2006.01)

(52) U.S. Cl.
CPC .......... *A61H 1/0266* (2013.01); *A61B 5/4836* (2013.01); *A61H 2001/0207* (2013.01);
(Continued)

(58) Field of Classification Search
CPC .......... A61H 1/0266; A61H 2001/0207; A61H 2001/1238; A61H 2001/1642; A61H 2001/1671; A61H 2203/0437
See application file for complete search history.

(56) References Cited

U.S. PATENT DOCUMENTS 5,453,082 A   9/1995   Lamont
6,010,468 A *  1/2000   Grove ................. A61H 1/0266
                                                    601/23

(Continued)

FOREIGN PATENT DOCUMENTS

BE    1014074 A3    3/2003

OTHER PUBLICATIONS

International Search Report and Written Opinion mailed Jul. 20, 2021 in PCT/US2021/027687 (10 pages).
(Continued)

*Primary Examiner* — Samchuan C Yao
*Assistant Examiner* — Nathan M Le
(74) *Attorney, Agent, or Firm* — Meunier Carlin & Curfman LLC (57) ABSTRACT

Various implementations include a method of decreasing oxygen saturation levels in a patient, including securing a leg and foot of the patient to a splint having a leg supporting portion, a foot supporting portion, and an inflatable device. The leg supporting portion includes a leg support body and leg support surface. The foot supporting portion includes a foot support body and foot support surface. The inflatable device rotates the foot support surface relative to the leg support surface from a first position to a second position. The angle between a leg longitudinal axis and a foot longitudinal axis is less in the second position than in the first position. The method further includes inflating the inflatable device to rotate the foot support surface from the first position to the second position and maintaining the second position to decrease oxygen saturation levels in the patient.

18 Claims, 8 Drawing Sheets

(52) U.S. Cl.
CPC ............... *A61H 2201/1238* (2013.01); *A61H 2201/1642* (2013.01); *A61H 2201/1671* (2013.01); *A61H 2203/0437* (2013.01); *A61H 2209/00* (2013.01)

(56) References Cited

U.S. PATENT DOCUMENTS

| | | | | |
|---|---|---|---|---|
| 6,110,078 | A * | 8/2000 | Dyer | .................. A61H 1/0266 482/121 |
| 7,833,184 | B2 * | 11/2010 | Chiodo | .................. A61F 5/012 601/151 |
| 2004/0005972 | A1 | 1/2004 | Sugiyama et al. | |
| 2007/0066465 | A1 | 3/2007 | Pisciottano | |
| 2012/0065564 | A1 * | 3/2012 | Hoffmeier | ................. A61F 5/58 602/28 |
| 2014/0214044 | A1 | 7/2014 | Robinson | |
| 2015/0080328 | A1 | 3/2015 | Villarreal et al. | |
| 2015/0265450 | A1 | 9/2015 | Rodgers | |
| 2019/0159728 | A1 | 5/2019 | Pritchard et al. | |
| 2019/0192327 | A1 * | 6/2019 | Sutti | .................... A61H 1/0266 |
| 2019/0350997 | A1 | 11/2019 | Tarnopolsky | |

OTHER PUBLICATIONS

International Preliminary Report on Patentability for International Application No. PCT/US2021/027887 dated Oct. 27, 2022, 9 pages.
Extended European Search Report in Application No. 21788328.9 dated May 13, 2024, 9 pages.

* cited by examiner

DIAGNOSTIC AND THERAPEUTIC SPLINTS AND METHODS OF USE

CROSS-REFERENCE TO RELATED APPLICATIONS

This application claims the benefit of U.S. Provisional Patent Application No. 63/011,587, filed Apr. 17, 2020, the contents of which are incorporated herein by reference in their entirety.

BACKGROUND

Patients with peripheral arterial disease (PAD) often have walking impairment and pain during walking (claudication) due to insufficient oxygen supply to leg muscles. Existing clinical treatment of PAD involves walking programs or revascularization. Surgery can carry significant costs and risks of acute complications from, for instance, recurrences due to restenosis or graft occlusion. Adherence to long-term walking programs can be difficult for frail patients such as the elderly. It is with respect to these and other considerations that the various embodiments described below are presented.

SUMMARY

Various implementations include a method of decreasing oxygen saturation levels in a patient. The method includes securing a leg and foot of the patient to a splint for diagnostic and/or therapeutic functions for a patient with a vascular impairment. The splint includes a leg supporting portion, a foot supporting portion, and an inflatable device. The leg supporting portion includes a leg support body and a leg support surface. The leg support surface is configured to support and secure the leg of the patient and has a leg longitudinal axis. The foot supporting portion includes a foot support body and a foot support surface. The foot support surface is configured to support and secure a portion of the foot of the patient and has a foot longitudinal axis. The inflatable device is for rotating the foot support surface relative to the leg support surface from a first position to a second position. An angle between the leg longitudinal axis and the foot longitudinal axis is less in the second position than in the first position. The method further includes inflating the inflatable device to rotate the foot support surface from the first position to the second position and maintaining the foot support surface in the second position to decrease oxygen saturation levels in the patient.

In some implementations, the method further includes maintaining the foot support surface in the second position until an oxygen saturation level of the patient is 74.6% or less.

In some implementations, the method further includes maintaining the foot support surface in the second position for 10 minutes or more.

In some implementations, the foot support surface includes the inflatable device. In some implementations, the foot support surface includes an insole. In some implementations, the inflatable device is affixed to the foot support body.

In some implementations, the splint further includes a pump configured to cause air to flow into the inflatable device to inflate the inflatable device.

In some implementations, the angle in the second position is 2 degrees or more degrees less than the angle in the first position. In some implementations, the angle in the first position is 70 degrees or greater. In some implementations, the angle in the second position is 68 degrees or greater.

In some implementations, the method further includes straightening a knee of the leg of the patient while the patient is in an upright seated position prior to remaining in the second position.

In some implementations, the splint further includes one or more straps spanning between the leg supporting portion and the foot supporting portion configured to maintain the foot longitudinal axis at a fixed acute angle with respect to the leg longitudinal axis in the first position.

Various other implementations include a method of improving delivery of a supplement to a target treatment location in a patient. The method includes securing a leg and foot of the patient to a splint for diagnostic and/or therapeutic functions for a patient with a vascular impairment. The splint includes a leg supporting portion, a foot supporting portion, and an inflatable device. The leg supporting portion includes a leg support body and a leg support surface. The leg support surface is configured to support and secure the leg of the patient and has a leg longitudinal axis. The foot supporting portion includes a foot support body and a foot support surface. The foot support surface is configured to support and secure a portion of the foot of the patient and has a foot longitudinal axis. The inflatable device is for rotating the foot support surface relative to the leg support surface from a first position to a second position. The angle between the leg longitudinal axis and the foot longitudinal axis is less in the second position than in the first position. The method further includes inflating the inflatable device to rotate the foot support surface from the first position to the second position and administering a supplement to the patient.

In some implementations, the supplement includes creatine monohydrate. In some implementations, the supplement includes a diabetic drug. In some implementations, the supplement includes a cocoa supplement. In some implementations, the supplement includes resveratrol. In some implementations, the supplement includes a dietary nitrate supplement.

In some implementations, the foot support surface includes the inflatable device. In some implementations, the foot support surface includes an insole. In some implementations, the inflatable device is affixed to the foot support body.

In some implementations, the splint further includes a pump configured to cause air to flow into the inflatable device to inflate the inflatable device.

In some implementations, the angle in the second position is 2 degrees or more degrees less than the angle in the first position. In some implementations, the angle in the first position is 70 degrees or greater. In some implementations, the angle in the second position is 68 degrees or greater.

In some implementations, the method further includes straightening a knee of the leg of the patient while the patient is in an upright seated position prior to remaining in the second position.

In some implementations, maintaining the foot support surface in the second position to decrease oxygen saturation levels in the patient. In some implementations, the method further includes maintaining the foot support surface in the second position until an oxygen saturation level of the patient is 74.6% or less. In some implementations, the method further includes maintaining the foot support surface in the second position for 10 minutes or more.

In some implementations, the splint further includes one or more straps spanning between the leg supporting portion and the foot supporting portion configured to maintain the foot longitudinal axis at a fixed acute angle with respect to the leg longitudinal axis in the first position.

Various other implementations include a splint for diagnostic and/or therapeutic functions for a patient with a vascular impairment. The splint includes a leg supporting portion, a foot supporting portion, and an inflatable device. The leg supporting portion includes a leg support body and a leg support surface. The leg support surface is configured to support and secure a leg of the patient and has a leg longitudinal axis. The foot supporting portion includes a foot support body and a foot support surface. The foot support surface is configured to support and secure a portion of a foot of the patient and has a foot longitudinal axis. The inflatable device is for rotating the foot support surface relative to the leg support surface from a first position to a second position. The angle between the leg longitudinal axis and the foot longitudinal axis is less in the second position than in the first position.

In some implementations, the foot support surface includes the inflatable device. In some implementations, the foot support surface includes an insole. In some implementations, the inflatable device is affixed to the foot support body.

In some implementations, the splint further includes a pump configured to cause air to flow into the inflatable device to inflate the inflatable device.

In some implementations, the angle in the second position is 2 degrees or more degrees less than the angle in the first position.

In some implementations, the splint further includes one or more straps spanning between the leg supporting portion and the foot supporting portion configured to maintain the foot longitudinal axis at a fixed acute angle with respect to the leg longitudinal axis in the first position.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

The devices, systems, and methods disclosed herein provide for a splint for diagnostic and/or therapeutic functions for a patient with a vascular impairment. The splint includes a leg supporting portion, a foot supporting portion, and an inflatable device. The leg supporting portion and the foot supporting portion are set at an angle relative to each other in a first position. The inflatable device can be inflated to rotate the foot of the patient acutely toward the patient's leg to a second position. The angle of the leg supporting portion relative to the foot supporting portion induce an ischemic state in the leg of the patient. The body of the patient reacts to the induced ischemic state by attempting to increase the patient's oxygen saturation levels. Once the device is returned to the first position, the ischemic state ends, but the body continues to increase the patient's oxygen saturation levels.

Various implementations include a splint for diagnostic and/or therapeutic functions for a patient with a vascular impairment. The splint includes a leg supporting portion, a foot supporting portion, and an inflatable device. The leg supporting portion includes a leg support body and a leg support surface. The leg support surface is configured to support and secure a leg of the patient. The leg support surface has a leg longitudinal axis. The foot supporting portion includes a foot support body and a foot support surface. The foot support surface is configured to support and secure a portion of a foot of the patient. The foot support surface has a foot longitudinal axis. The inflatable device is for rotating the foot support surface relative to the leg support surface from a first position to a second position. The angle between the leg longitudinal axis and the foot longitudinal axis is less in the second position than in the first position.

Various other implementations include a method of decreasing oxygen saturation levels in a patient. The method includes (1) securing a leg and foot of the patient to a splint, such as the splint described above, for diagnostic and/or therapeutic functions for a patient with a vascular impairment, (2) inflating the inflatable device to rotate the foot support surface from the first position to the second position, and (3) maintaining the foot support surface in the second position to decrease oxygen saturation levels in the patient.

Various other implementations include a method of improving delivery of a supplement to a target treatment location in a patient. The method includes (1) securing a leg and foot of the patient to a splint, such as the splint described above, for diagnostic and/or therapeutic functions for a patient with a vascular impairment, (2) inflating the inflatable device to rotate the foot support surface from the first position to the second position, and (3) administering a supplement to the patient.

Figure 1:
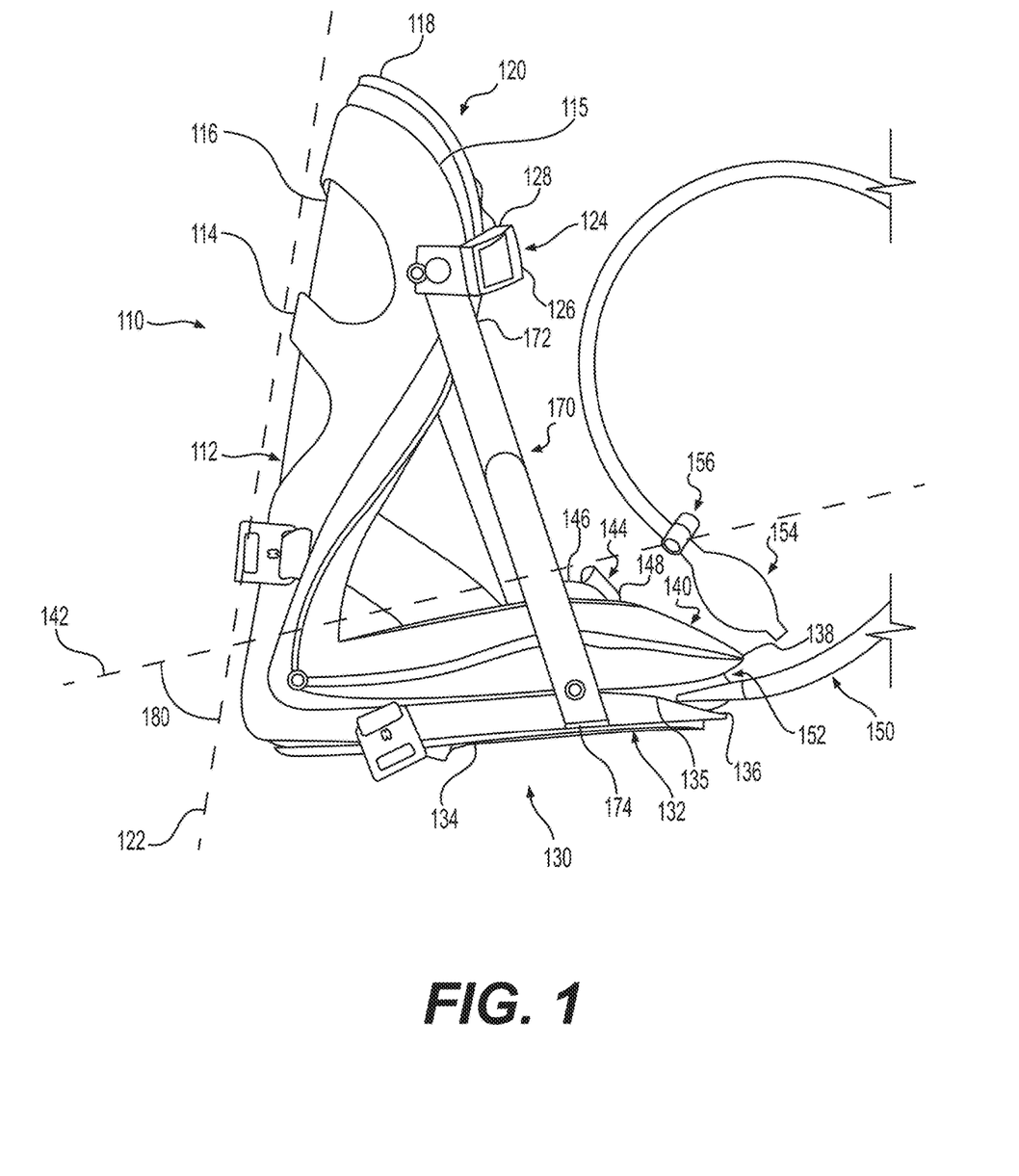
FIG. 1 is side view of a splint in the first position, according to one implementation.
Figure 2:
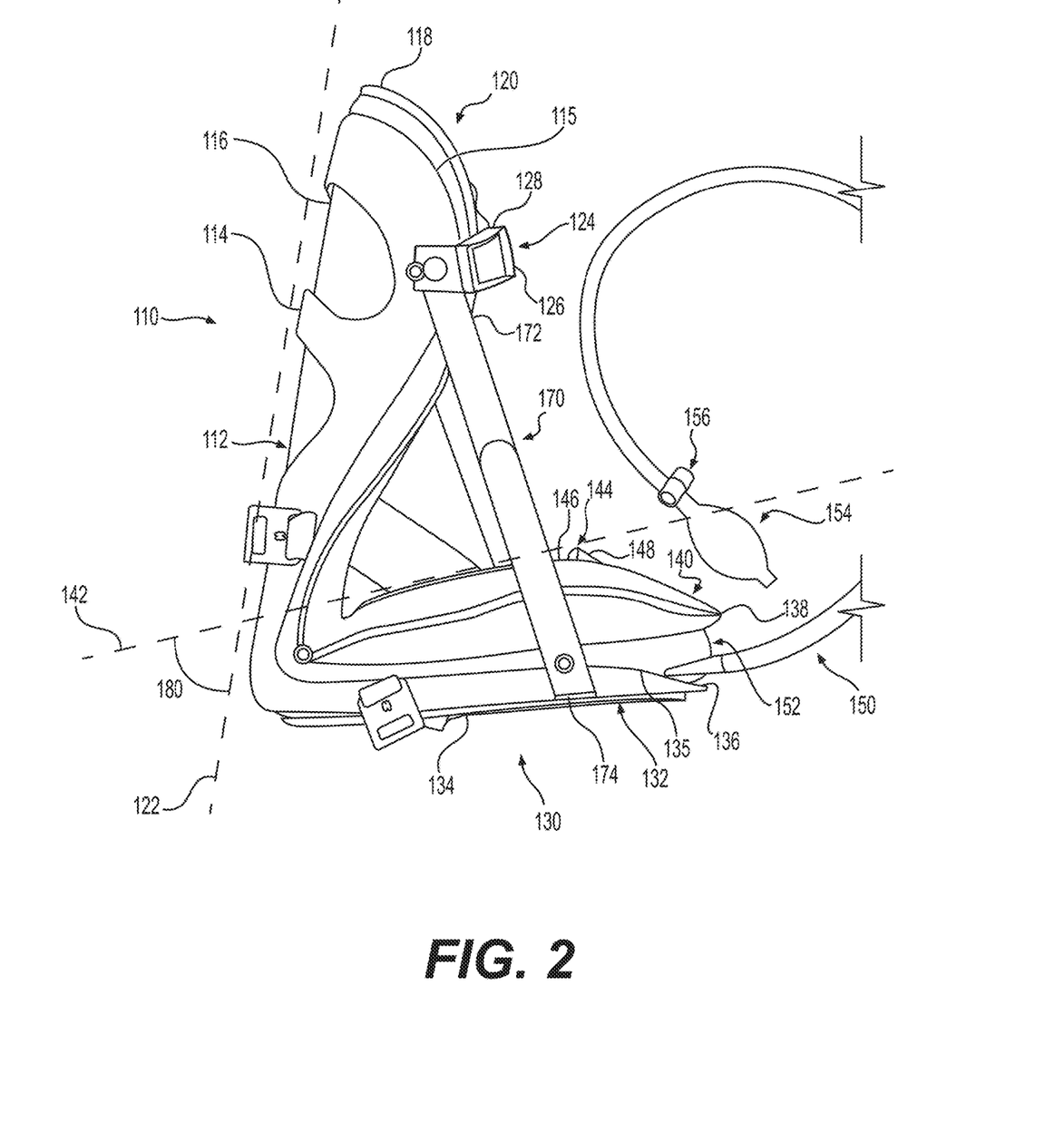
FIG. 2 is side view of the splint of FIG. 1 in the second position.

FIGS. 1 and 2 show an implementation of a splint 100 for diagnostic and/or therapeutic functions for a patient with a vascular impairment. The splint 100 includes a leg supporting portion 110, a foot supporting portion 130, two side straps 170, and an inflatable device 150.

The leg supporting portion 110 includes a leg support body 112, a leg support surface 120, and a plurality of leg support straps 124. The leg support body 112 includes a plastic rigid shell 114 and an inner liner 118. The plastic rigid shell 114 of the leg supporting portion 110 has an inner surface 116 that is shaped to receive the inner liner 118 of the leg supporting portion 110. The inner liner 118 defines a leg support surface 120 that is sized to support and secure a portion of the leg of a patient. The inner liner 118 provides a cushion between the leg of the patient and the leg supporting portion 110. The leg supporting portion 110 is rigid enough to ensure that the portion of the leg of the patient is supported and secured by the leg support surface 120 of the inner liner 118 such that a leg longitudinal axis 122 of the leg support surface 120 can be maintained during use.

Although the leg supporting portion 110 shown in FIGS. 1 and 2 includes a plastic rigid shell 114 and an inner liner 118, in some implementations, the inner liner is combined with the plastic rigid shell such that the plastic rigid shell and inner liner are a single component. In some implementations, the leg supporting portion only includes a plastic rigid shell and no inner liner. Although the inner liner 118 shown in FIGS. 1 and 2 defines the leg support surface 120, in some implementations, the leg support surface is defined by any other portion of the leg supporting portion. Although the rigid shell 114 shown in FIGS. 1 and 2 is made from plastic, in some implementations, the rigid shell is made from any type of polymer, metal, wood, or any other material or combination of materials rigid enough to ensure that the portion of the leg of the patient is supported and secured by the leg support surface of the inner liner such that a leg longitudinal axis of the leg support surface can be maintained during use. The inner liner 118 of the leg supporting portion 110 is made from a foam, but in some implementations, the inner liner is made from any resilient material capable of providing a cushion between the leg of the patient and the plastic rigid shell such that the plastic rigid shell does not cause bruising, bleeding, or other injuries to the portion of the leg of the patient during use.

Each end of each of the plurality of leg support straps 124 is coupled adjacent to one of the opposing longitudinal edges 115 of the plastic rigid shell 114. The plurality of leg support straps 124 are spaced apart from each other along the longitudinal edges 115 of the plastic rigid shell. The plurality of leg support straps 124 include a web 126 and a buckle 128. The web 126 extends through openings defined by the buckle 128 such that the web 126 is slidingly coupled to the buckle 128. Because the web 126 is slidingly coupled to the buckle 128, the length of the plurality of leg support straps 124 as measured between opposite longitudinal edges 115 of the plastic rigid shell 114 is selectively adjustable. The buckle 128 can also be unbuckled to easily allow the leg of the patient to be removed from the splint 100 without adjusting the length of the plurality of leg support straps 124.

The foot supporting portion 130 includes a foot support body 132, a foot support surface, and a foot support strap 144. The foot support body 132 includes a plastic rigid shell 134 and an insole 138. The plastic rigid shell 134 of the foot support body 132 has an inner surface 136 that is shaped to receive the insole 138 of the foot support body 132. The insole 138 defines a foot support surface 140 that is sized to support and secure a portion of the foot of a patient. The insole 138 provides a cushion between the foot of the patient and the foot support body 132. The foot support body 132 is rigid enough to ensure that the portion of the foot of the patient is supported and secured by the foot support surface 140 of the insole 138 such that a foot longitudinal axis 142 of the foot support surface 140 can be maintained during use. The foot supporting portion 130 is pivotably coupled to the leg supporting portion 110, and an angle 180 is defined between the leg longitudinal axis 122 and the foot longitudinal axis 142.

Although the foot support body 132 shown in FIGS. 1 and 2 includes a plastic rigid shell 134 and an insole 138, in some implementations, the insole is combined with the plastic rigid shell such that the plastic rigid shell and insole are a single component. In some implementations, the foot support body only includes a plastic rigid shell and no insole. Although the insole 138 shown in FIGS. 1 and 2 defines the foot support surface 140, in some implementations, the foot support surface is defined by any other portion of the foot supporting portion. Although the rigid shell 134 shown in FIGS. 1 and 2 is made from plastic, in some implementations, the rigid shell is made from any type of polymer, metal, wood, or any other material or combination of materials rigid enough to ensure that the portion of the foot of the patient is supported and secured by the foot support surface of the insole such that a foot longitudinal axis of the foot support surface can be maintained during use. The insole 138 of the foot support body 132 is made from a foam, but in some implementations, the insole is made from any resilient material capable of providing a cushion between the foot of the patient and the plastic rigid shell such that the plastic rigid shell does not cause bruising, bleeding, or other injuries to the portion of the foot of the patient during use.

Each end of the foot support strap 144 is coupled adjacent to one of the opposing longitudinal edges 135 of the plastic rigid shell 134. The foot support strap 144 includes a web 146 and a buckle 148. The web 146 extends through openings defined by the buckle 148 such that the web 146 is slidingly coupled to the buckle 148. Because the web 146 is slidingly coupled to the buckle 148, the length of the foot support strap 144 as measured between opposite longitudinal edges 135 of the plastic rigid shell 134 is selectively adjustable. The buckle 148 can also be unbuckled to easily allow the foot of the patient to be removed from the splint 100 without adjusting the length of the foot support strap 144.

The two side straps 170 shown in FIGS. 1 and 2 are made of a web. Each of the two side straps 170 has a first end 172 and a second end 174. The first end 172 of each side strap 170 is coupled to the leg support body 112 of the leg supporting portion 110 and the second end 174 of each side strap 170 is coupled to the foot support body 132 of the foot supporting portion 130. The length of the side straps 170, as measured from the coupling point of the first ends 172 of the side straps 170 to the second ends 174 of the side straps 170 is adjustable. Because the leg supporting portion 110 and the foot supporting portion 130 are pivotably coupled to each other, adjustment of the side straps 170 selectively adjusts the angle 180 defined between the leg longitudinal axis 122 and the foot longitudinal axis 142.

The inflatable device 150 includes a bladder 152 and a pump 154. The bladder 152 of the inflatable device 150 is coupled to the inner surface 136 of the rigid shell 134 of the foot supporting portion 130 and is disposed between the inner surface 136 of the rigid shell 134 of the foot supporting portion 130 and the insole 138. The pump 154 is removably coupled to, and in fluid communication with, the bladder 152. The pump 154 can be actuated to cause air to flow from the environment into the bladder 152. The pump 154 also includes a releasable one-way valve 156 to selectively prevent the backflow of air from the bladder 152 back to the environment.

As the bladder 152 of the inflatable device 150 is filled with air, the foot support surface 140 defined by the insole 138 of the foot supporting portion 130 is rotated relative to the leg support surface 120 defined by the inner liner 118 of the leg supporting portion 110 from a first position (shown in FIG. 1) to a second position (shown in FIG. 2). The angle 180 defined between the leg longitudinal axis 122 and the foot longitudinal axis 142 when the splint is in the first position is set by configuring the side straps 170 in a clinical setting to ensure the angle 180 in the first position is within 2-3 degrees of a verified angle for inducing an ischemic condition in the patient. The patient is instructed in a clinical setting to apply a predetermined number of pumps (e.g., 1-10 pumps) to the pump 154 of the inflatable device 150 that have been determined to induce the ischemic condition. After the predetermined number of pumps have been applied, the splint is in the second position. Thus, when the inflatable device 150 rotates the foot support surface 140 relative to the leg support surface 120 from the first position to the second position, the angle 180 of the foot longitudinal axis 142 relative to the leg longitudinal axis 122 decreases. Because the pump 154 includes a releasable one-way valve 156, the inflation of the bladder 152, and thus the second position, can be maintained indefinitely. The releasable one-way valve 156 can then be actuated to allow the air to exhaust from the bladder 152 back to the environment such that the splint 100 can rotate back from the second position to the first position. In the first position of the splint, the angle 180 is 70 degrees, but in some implementations, the angle is greater than 70 degrees. In the second position of the splint, the angle 180 is 68 degrees, but in some implementations, the angle is greater than 68 degrees. In some implementations, the angle is in the range of 68 degrees to 73 degrees. In FIGS. 1 and 2, the angle 180 in the second position is at least 2 degrees less than the angle 180 in the first position, but in some implementations, the angle in the second position is 2 or more degrees less than the angle in the first position (e.g., 3, 4, or 5 degrees less than the angle in the first position). In some implementations, the angle 180 is 70.34 degrees when the splint is in the first position. In some implementations, the angle 180 is 68.33±2.51 degrees when the splint is in the second position.

Although the bladder 152 shown in FIGS. 1 and 2 is coupled to the inner surface 136 of the rigid shell 134 of the foot supporting portion 130, in some implementations, the bladder is coupled to the insole, either directly or indirectly, or to any other portion of the foot supporting portion that would cause the foot longitudinal axis to rotate relative to the leg longitudinal axis when the device is moved from the first position to the second position. In some implementations, the bladder is coupled indirectly to the foot supporting portion. In some implementations, the inflatable device is not coupled to the foot supporting portion, and the inflatable device may rely on friction to hold the bladder in place during use. In some implementations, the bladder defines the foot support surface. In some implementations, the inflatable device does not include a pump or the pump is integrally coupled to the bladder. The pump 154 shown in FIGS. 1 and 2 is a manually actuated pump 154, but in other implementations, the pump is an electrically, pneumatically, or hydraulically actuated pump. Although the pump 154 shown in FIGS. 1 and 2 is configured to cause air from the environment to flow into the bladder 152, in other implementations, the pump is configured to cause any other fluid to flow into the bladder. Although the pump 154 shown in FIGS. 1 and 2 includes a releasable one-way valve, in some implementations, the bladder includes the releasable one-way valve.

Figure 3:
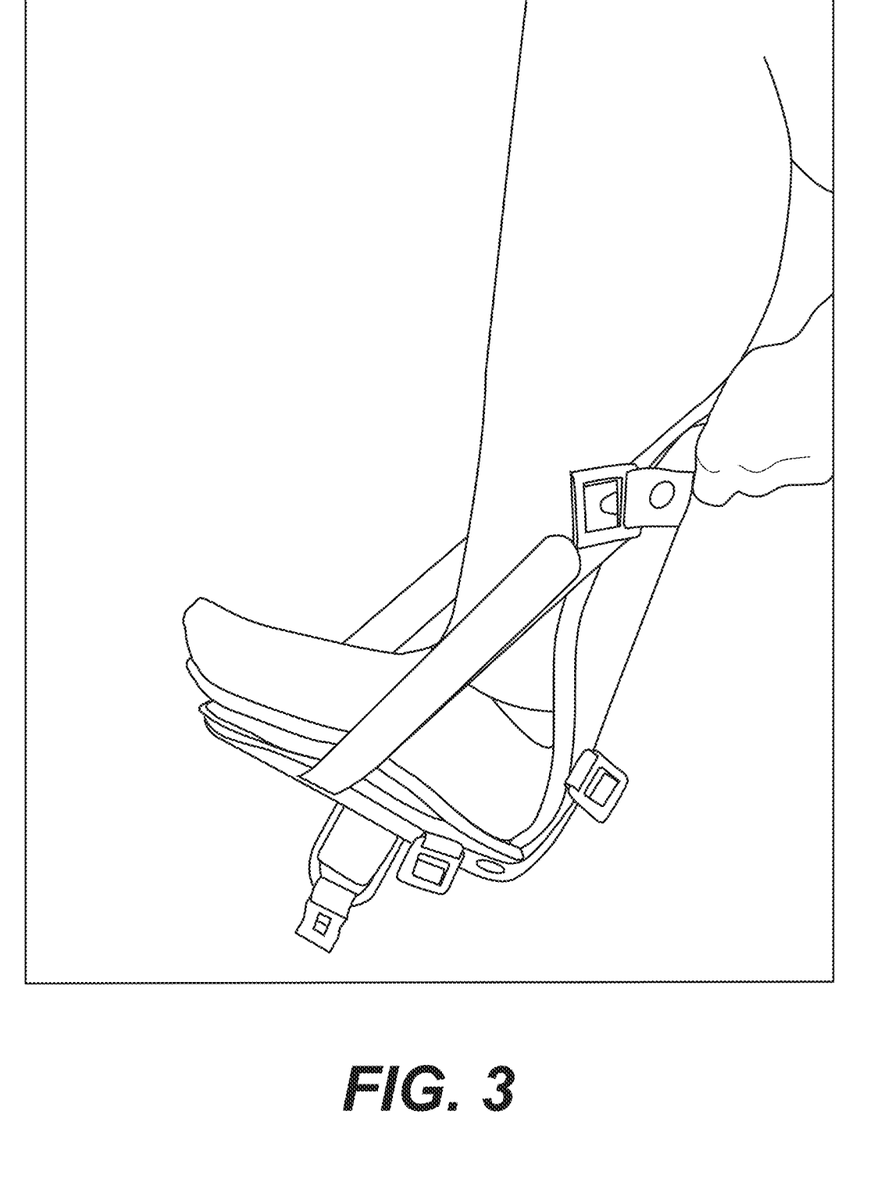
FIG. 3 is perspective view of the foot and leg of a patient being disposed within the splint of FIG. 1.
Figure 4:
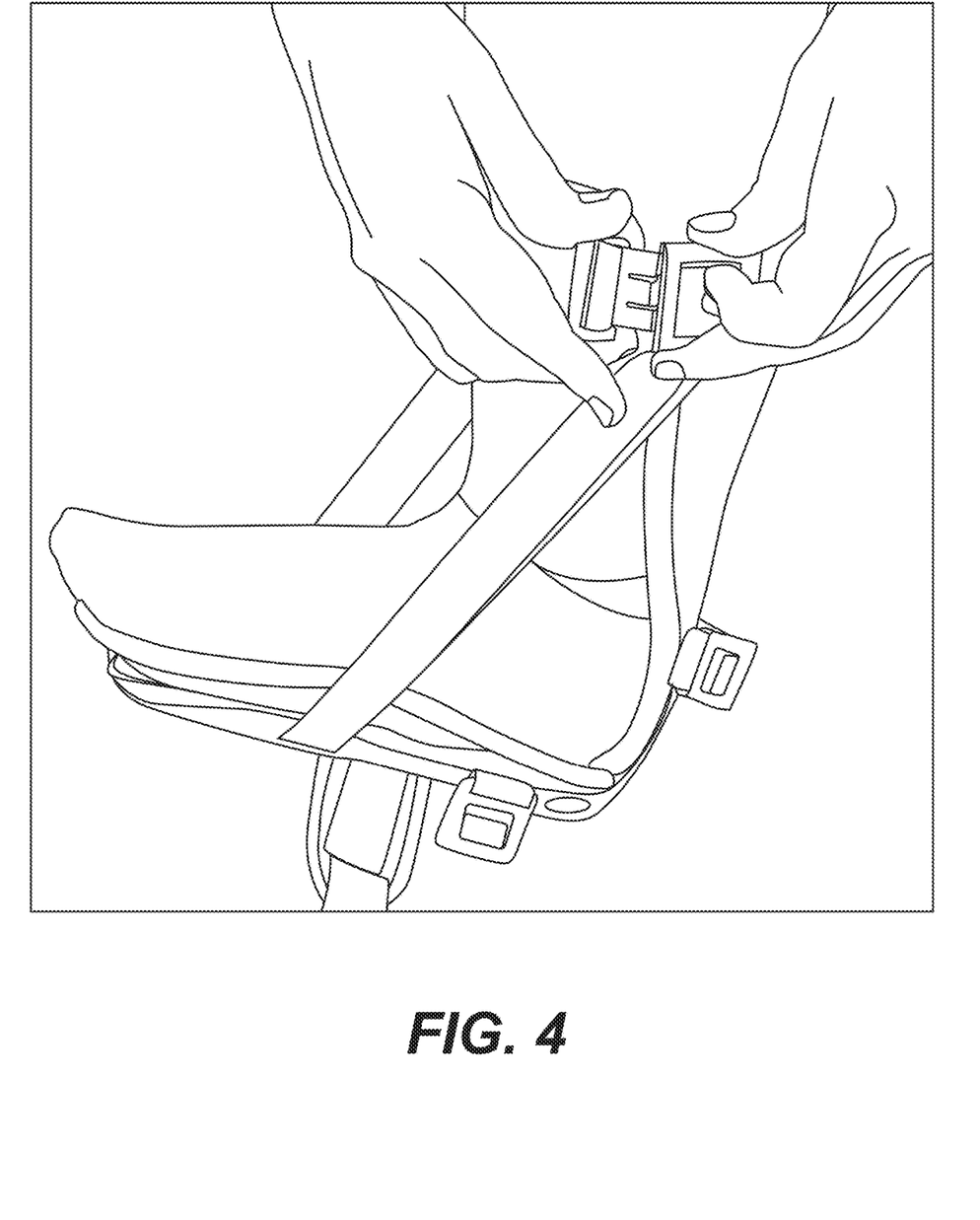
FIG. 4 is perspective view of the splint of FIG. 1 being secured to the foot and leg of a patient.
Figure 5:
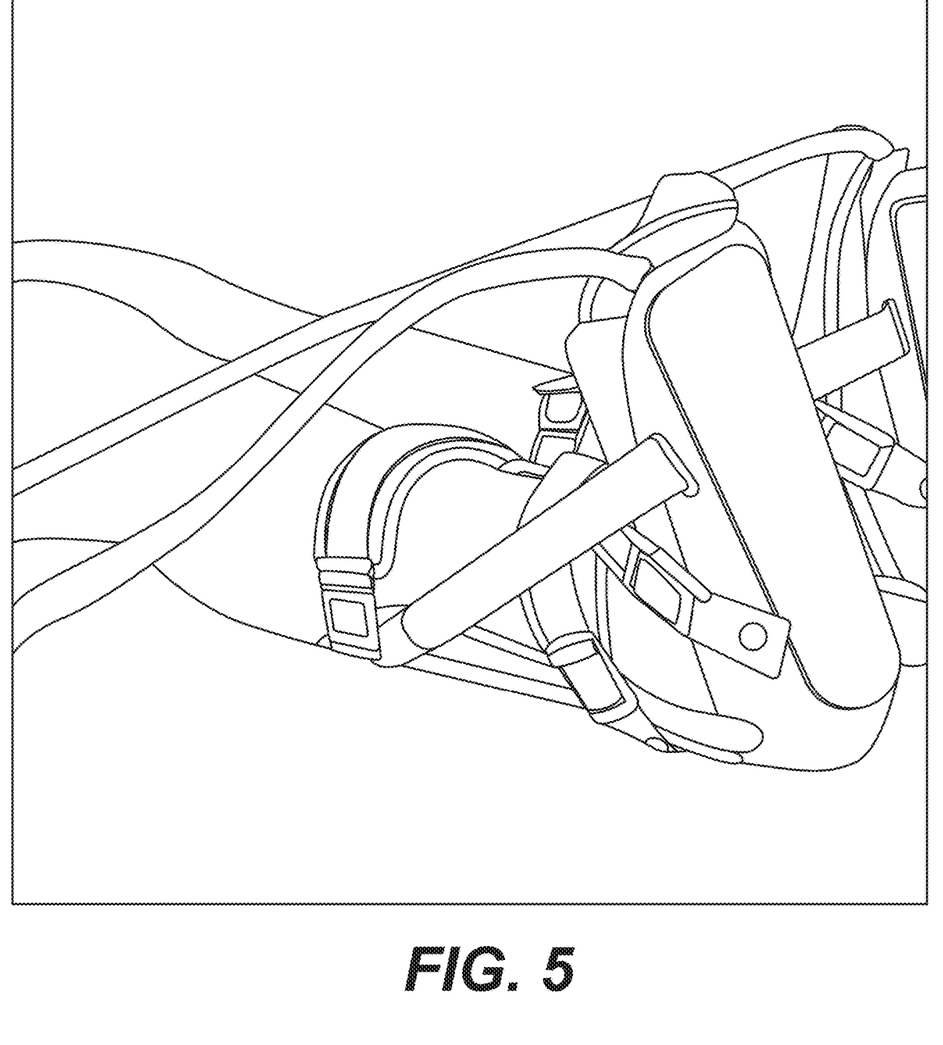
FIG. 5 is perspective view a patient oriented in the seated position wearing the splint of FIG. 1.
Figure 6:
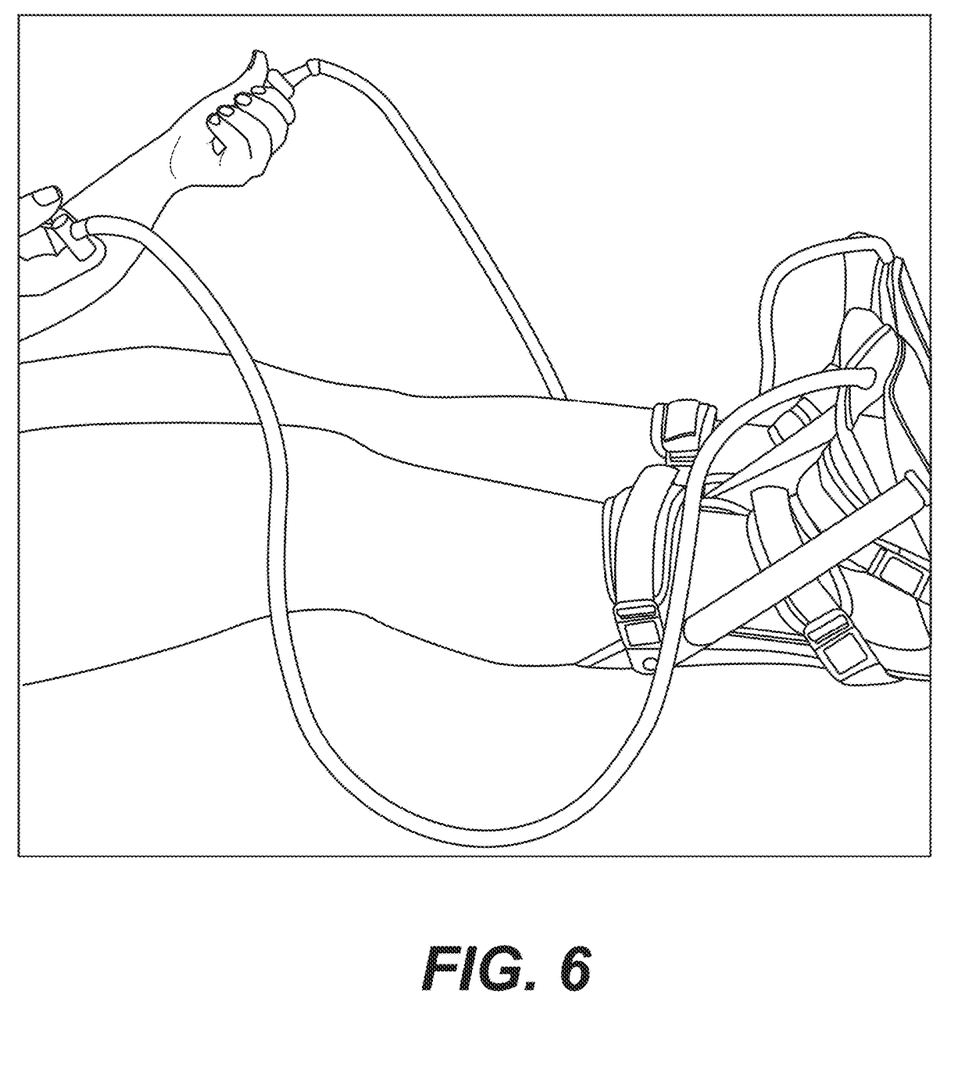
FIG. 6 is perspective view of the inflatable device of the splint of FIG. 1 being inflated.
Figure 7:
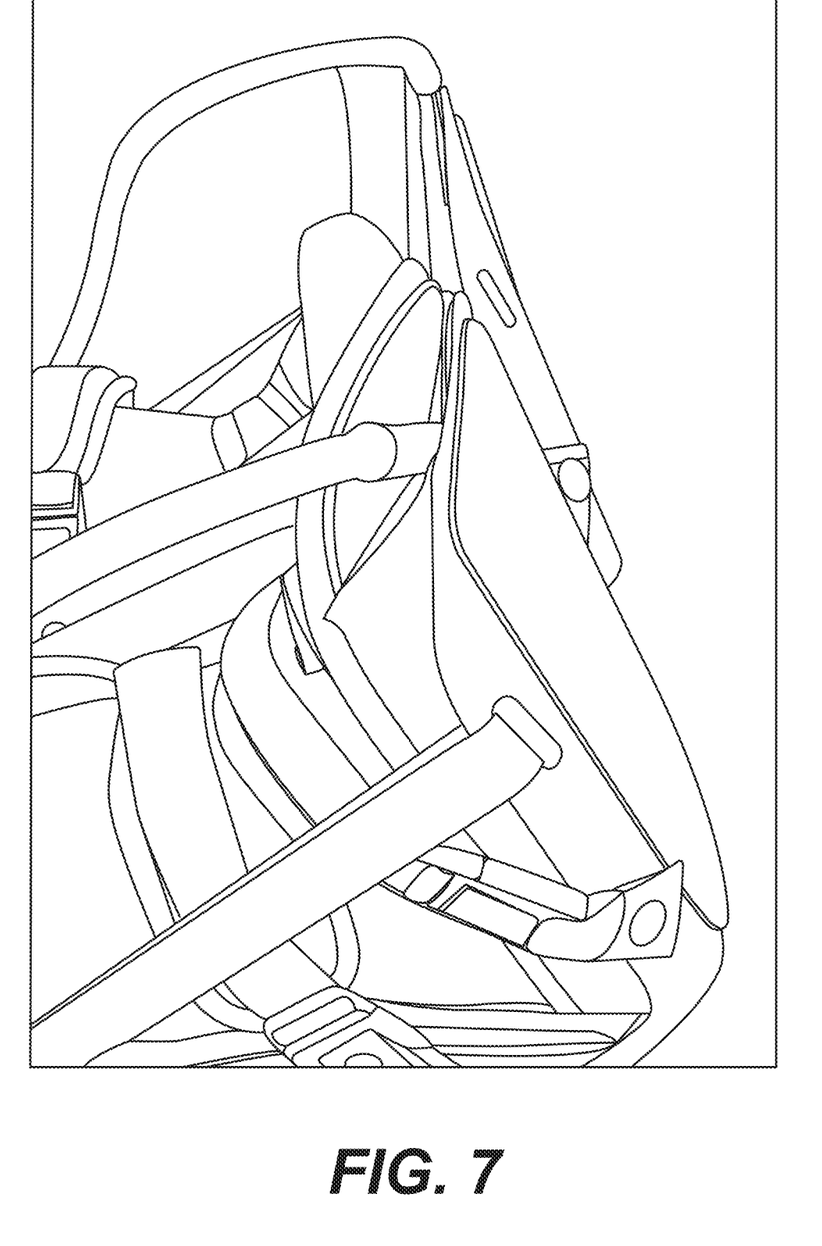
FIG. 7 is perspective view of the splint of FIG. 1 in the first position.
Figure 8:
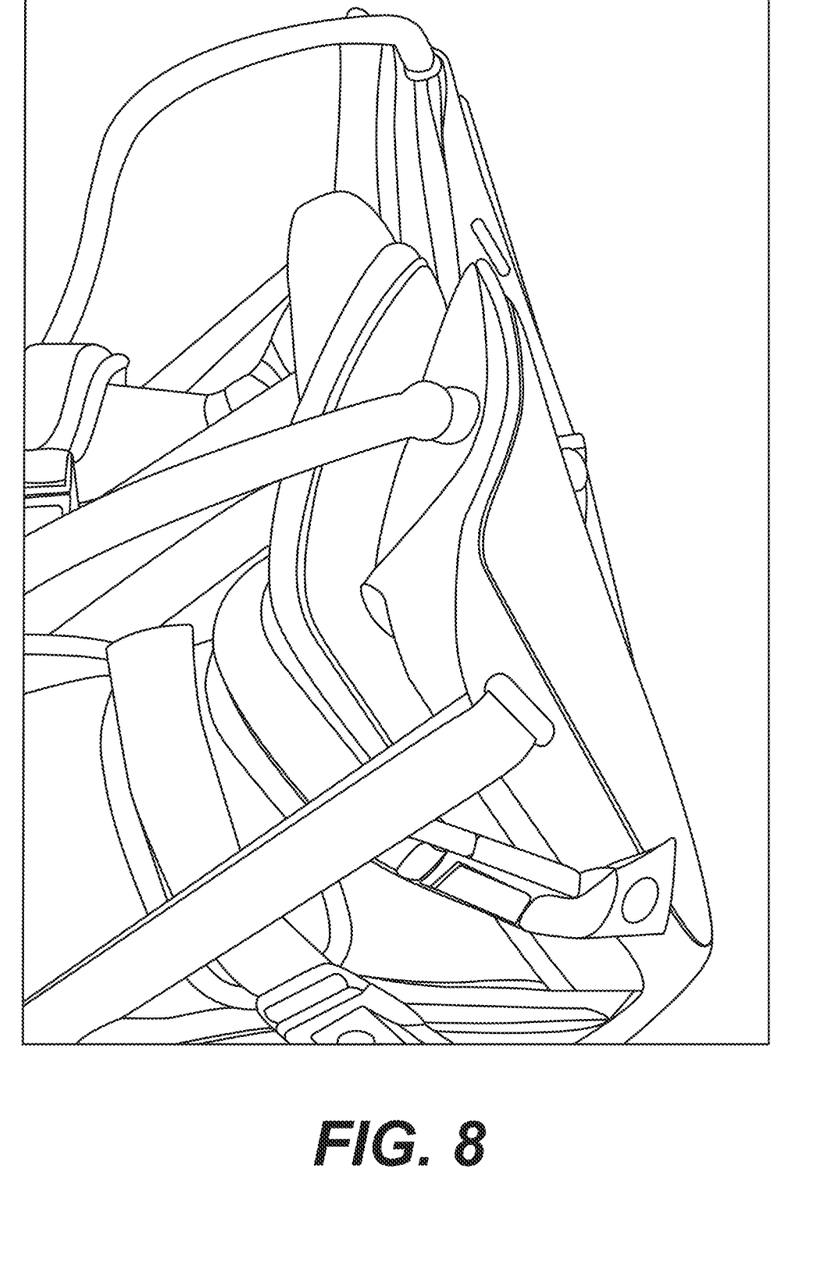
FIG. 8 is perspective view of the splint of FIG. 1 in the second position.

The splint 100 can be used to decrease oxygen saturation levels in a patient. The patient first places the patient's leg in the splint 100 such that a portion of the patient's foot contacts the foot support surface 140 and a portion of the patient's leg contacts the leg support surface 120, as shown in FIG. 3. The splint 100 is then secured to leg and foot of the patient by fastening the plurality of leg support straps 124 and the foot support strap 144, as shown in FIG. 4. The patient is then positioned in a seated position with the patient's back at a 90-degree angle to the patient's leg and with the patient's knee straightened, as shown in FIG. 5. The side straps 170 of the splint 100 are adjusted such that the splint 100 is in the first position. The angle 180 defined between the leg longitudinal axis 122 and the foot longitudinal axis 142 when the splint is in the first position is set by configuring the side straps 170 in a clinical setting to ensure the angle 180 in the first position is within 2-3 degrees of a verified angle for inducing an ischemic condition in the patient. As shown in FIG. 6, the pump 154 is then actuated to inflate the bladder 152 of the inflatable device 150. The inflation of the bladder 152 of the inflatable device 150 rotates the foot support surface 140 from the first position (shown in FIG. 7) to the second position (shown in FIG. 8). The foot support surface 140 is maintained in the second position for a predetermined period of time to decrease oxygen saturation levels in the patient. The predetermined period of time for maintaining the device in the second position can be 5 minutes or more, 10 minutes or more, 15 minutes or more, 20 minutes or more, 25 minutes or more, or 30 minutes or more. The purpose of maintaining the device in the second position for a predetermined period of time is to cause an ischemic state in the leg muscles of the patient until the oxygen saturation level of the patient is 74.6% or less. This causes the patient's body to attempt to correct for the lowered oxygen saturation level. Once the oxygen saturation level of the patient is maintained at a sufficiently low level for the predetermined amount of time, the device is returned to the first position shown in FIG. 7. However, the patient's body continues to increase the oxygen saturation level in response to the previously induced ischemic state.

In some implementations, the baseline oxygen saturation level of the patient is 79.5% or higher. In some implementations, the baseline oxygen saturation level of the patient is in the range of 79.5% to 88.5%. In some implementations, the oxygen saturation level of the patient is 79.6% or less after the second position is maintained for a period of time of 5 minutes. In some implementations, the oxygen saturation level of the patient is in the range of 70.4% to 79.6% after the second position is maintained for a period of time of 5 minutes. Although the oxygen saturation level of the patient is 74.6% or less after maintaining the device in the second position for a predetermined period of time of 10 minutes, in some implementations, the oxygen saturation level of the patient after maintaining the device in the second position for a predetermined period of time of 10 minutes is in the range of is 67.4% to 74.6%.

The splint 100 can also be used to improve the delivery of a supplement to a target treatment location in a patient. The patient first places the patient's leg in the splint 100 such that a portion of the patient's foot contacts the foot support surface 140 and a portion of the patient's leg contacts the leg support surface 120, as shown in FIG. 3. The splint 100 is then secured to leg and foot of the patient by fastening the plurality of leg support straps 124 and the foot support strap 144, as shown in FIG. 4. The patient is then positioned in a seated position with the patient's back at a 90-degree angle to the patient's leg and with the patient's knee straightened, as shown in FIG. 5. The side straps 170 of the splint 100 are adjusted such that the splint 100 is in the first position. The angle 180 defined between the leg longitudinal axis 122 and the foot longitudinal axis 142 when the splint is in the first position is set by configuring the side straps 170 in a clinical setting to ensure the angle 180 in the first position is within 2-3 degrees of a verified angle for inducing an ischemic condition in the patient. As shown in FIG. 6, the pump 154 is then actuated to inflate the bladder 152 of the inflatable device 150. The inflation of the bladder 152 of the inflatable device 150 rotates the foot support surface 140 from the first position (shown in FIG. 7) to the second position (shown in FIG. 8). A supplement is then administered to the patient while the device is in the second position. In some implementations, the supplement is administered independent of application of the splint 100, prior to administration of the splint 100, or following administration of the splint 100. In some implementations, the supplement is creatine monohydrate. In some implementations, the supplement is a diabetic drug, such as metformin. In some implementations, the supplement is a cocoa supplement. In some implementations, the supplement is resveratrol. In some implementations, the supplement is beet root juice or another dietary nitrate supplement. As discussed above, the ischemic state induced in the patient while in the second position causes the patient's body to attempt to correct for the lowered oxygen saturation level. Once the oxygen saturation level of the patient is sufficiently low, the device is returned to the first position shown in FIG. 7. However, the patient's body continues to increase the oxygen saturation level in response to the previously induced ischemic state. The increase in oxygen saturation level aids in the uptake of the administered supplement.

EXAMPLES

Below is the anatomical description of the target result desired by applying a stretch to aid in differentiating over similar splints that facilitate stretching for plantar fasciitis. Preliminary data confirms that muscle stretching preformed with the dorsiflexion splint induces a reduction in muscle oxygenation in the calf muscles (as measured in the gastrocnemius muscle) that can be measured with near-infrared spectroscopy (NIRS). The target result was to adjust the level of splint dorsiflexion to a setting that produces a tolerable level of stretch (without undue discomfort) that maximizes the decrease in muscle oxygenation.

In order to accomplish this result in older peripheral artery disease (PAD) patients who have varying levels of frailty or reduced flexibility, a device was created to allow patients to first secure the splint device on the foot at a pre-set, but less than maximal degree of dorsiflexion. The importance of this is two-fold: 1) the splint device is easier to secure with the foot on the floor before the legs are extended to produce maximal dorsiflexion, and 2) securing both splints when the splint is at a maximal level of dorsiflexion (i.e., it is difficult for the patient to push his heel completely back into the splint and secure the heel strap when the splint is in the maximal dorsiflexion position).

The final device configuration was achieved by having the patient secure the splints while they are set at an angle that is near (but is a few degrees less than maximal) the maximal level of dorsiflexion, and then allowing the patient to assume a seated position with both legs fully extended. Once the legs are extended, a bulb that is accessible at the level of the patient's thigh (i.e., easily reached in the seated, legs extended position) is then used to adjust the angle of dorsiflexion. For most patients, this final adjustment will increase the angle of dorsiflexion by 2-4 degrees, resulting in a level of stretch that is tolerable, but also maximal without undue discomfort. A portable MRS device was used to verify that this level of dorsiflexion produces a significant decrease in oxygenation in the gastrocnemius muscle. The goal was to use the device to produce muscle stretch-induced reduction of blood flow/oxygen delivery in order to stimulate adaptive responses in both the blood vessels and the muscle fibers over a period of repeated daily muscle stretching.

The splint was adjusted to a setting that allowed for securement on the foot by the patient alone, but at a level that requires only a minor adjustment, with the inflation device, to produce maximal stretch and maximal change in oxygenation. Patients were instructed in the correct use of the splints, including explanation of the correct anatomical position (seated with a straight back with legs fully extended in front of them at the same level as their hips). The side strap settings on the splint device were adjusted to produce near maximal stretch of the calf muscles and that setting will be marked, with the patient being instructed not to change those side strap settings. The final adjustment of the dorsiflexion angle was achieved with pumping, and the patient was instructed to use the same number of pumps each session. The change in oxygenation that occurred during static stretch was measured with NIRS.

Next, the improved quality of life was determined with an initial focus on long-term improvements to walking distances and a later focus on incorporating additional test results as completed, such as MRI results.

The following measures related to improved quality of life assess walking function, health events (especially those that include visits to the ER or hospital), physical function (e.g., activities of daily living) testing, cognitive function testing, and blood oxygen level dependent (BOLD) MRI of the brain:

A. The 6-minute walk test: In addition to measuring continuous walking distance, pain-free walking distance, and total walking distance, muscle oxygenation was monitored continuously during performance of the standardized 6-minute walk test using the Moxy (NIRS) system.

B. Health and exercise questionnaires: (1) The Walking Impairment Questionnaire, patient-reported walking performance specifically developed for PAD; (2) The Medical Outcomes Study Short Form-36, a record of medical outcomes; and (3) Functionality Testing (Activities of Daily Living), sub-domains of lower body strength, endurance, and balance and coordination.

The Functionality Testing included ten tasks that are administered, and a combination of time, distance, and weight is used to quantify performance. Tasks quantified using both weight and time include: (i) carrying a pot of weights and (ii) carrying groceries. Tasks quantified by time alone include: (iii) transferring laundry from a washer to a dryer, (iv) putting on and removing a jacket, (v) floor sweeping, (vi) climbing stairs, (vii) getting down and up from the floor, and (viii) picking up 4 scarves from the floor. Tasks that are quantified by distance alone include: (ix) a 6-minute walk and (x) highest reach. Each task is scored 0-100, based on an empirically derived range from data gathered on older adults with a broad range of individual functional abilities Time is used to calculate speed (1/t), so that higher numbers reflect higher function for each unit of measure (weight, distance, and speed). Each task is scaled 1 to 100 according to the following formula: Corrected Score= (observed score−lower limit)/(upper limit−lower limit)*100.

C. Cognitive function testing and quality of life assessment by questionnaires/paper tests include: (1) The Beck Depression Inventory-II; (2) Trails Making Tests (A, B); (3) Patient Health Questionnaire-9; and (4) World Health Organization Quality of Life-Brief Questionnaire.

D. Brain MR data acquisition and analysis: Structural brain images were sagittally acquired and functional images were acquired using a multi-band (MB) echo planar imaging (EPI) protocol before and after 4 weeks of stretching or placebo stretching. To relate brain connectivity to questionnaire or physiological measures, voxel-wise robust linear regression was performed in the R.

Lastly, the improved drug delivery (improvement based on improved blood flow/muscle profusion) was determined. A study was performed in which patients were enrolled to perform stretching alone or stretching while also taking creatine monohydrate as a supplement. The walking function with the 6-minute walk test was assessed, and muscle oxygenation during the walking test with NIRS was measured.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A method of decreasing oxygen saturation levels in a patient, the method comprising:
   securing a leg and foot of the patient to a splint for diagnostic and/or therapeutic functions for the patient with a vascular impairment, the splint comprising:
      a leg supporting portion including a leg support body and a leg support surface, the leg support surface being configured to support and secure the leg of the patient, the leg support surface having a leg longitudinal axis,
      a foot supporting portion including a foot support body and a foot support surface, the foot support surface being configured to support and secure a portion of the foot of the patient, the foot support surface having a foot longitudinal axis,
      one or more straps spanning between the leg supporting portion and the foot supporting portion configured to maintain the foot longitudinal axis at a fixed acute angle with respect to the leg longitudinal axis in a first position, wherein the one or more straps are adjustable to a first length to define the fixed acute angle between the leg longitudinal axis and the foot longitudinal axis in the first position; and
      an inflatable device for rotating the foot support surface relative to the leg support surface from the first position to a second position, wherein an angle between the leg longitudinal axis and the foot longitudinal axis is less in the second position than in the first position;
   inflating the inflatable device to rotate the foot support surface from the first position to the second position, wherein the angle between the leg longitudinal axis and the foot longitudinal axis in the second position is a verified angle for inducing an ischemic condition in the patient, the verified angle being preconfigured based on the first length of the one or more straps, inflation of the inflatable device, and a first oxygen saturation level of the patient; and
   maintaining the foot support surface in the second position to decrease oxygen saturation levels in the patient.

2. The method of claim 1, further comprising maintaining the foot support surface in the second position until the first oxygen saturation level of the patient is 74.6% or less.

3. The method of claim 1, further comprising maintaining the foot support surface in the second position for 10 minutes or more.

4. The method of claim 1, wherein the foot support surface comprises the inflatable device.

5. The method of claim 1, wherein the foot support surface comprises an insole.

6. The method of claim 1, wherein the inflatable device is affixed to the foot support body.

7. The method of claim 1, wherein the splint further comprises a pump configured to cause air to flow into the inflatable device to inflate the inflatable device.

8. The method of claim 1, wherein the angle in the second position is 2 degrees or more degrees less than the angle in the first position.

9. The method of claim 1, wherein the angle in the first position is 70 degrees or greater.

10. The method of claim 1, wherein the angle in the second position is 68 degrees or greater.

11. The method of claim 1, further comprising straightening a knee of the leg of the patient while the patient is in an upright seated position prior to remaining in the second position.

12. The method of claim 1, further comprising administering a supplement to the patient after inflating the inflatable device.

13. A splint for diagnostic and/or therapeutic functions for a patient with a vascular impairment, the splint comprising:
   a leg supporting portion including a leg support body and a leg support surface, the leg support surface being configured to support and secure a leg of the patient, the leg support surface having a leg longitudinal axis;
   a foot supporting portion including a foot support body and a foot support surface, the foot support surface being configured to support and secure a portion of a foot of the patient, the foot support surface having a foot longitudinal axis;
   one or more straps spanning between the leg supporting portion and the foot supporting portion configured to maintain the foot longitudinal axis at a fixed acute angle with respect to the leg longitudinal axis in a first position, the one or more straps being adjustable to a first length to define the fixed acute angle between the leg longitudinal axis and the foot longitudinal axis in the first position; and an inflatable device for rotating the foot support surface relative to the leg support surface from the first position to a second position, wherein an angle between the leg longitudinal axis and the foot longitudinal axis is less in the second position than in the first position, wherein the angle between the leg longitudinal axis and the foot longitudinal axis in the second position is a verified angle for inducing an ischemic condition in the patient, the verified angle being preconfigured based on the first length of the one or more straps, inflation of the inflatable device, and a first oxygen saturation level of the patient; and wherein the angle in the second position is in a range of 68 to 73 degrees.

14. The splint of claim 13, wherein the foot support surface comprises the inflatable device.

15. The splint of claim 13, wherein the foot support surface comprises an insole.

16. The splint of claim 13, wherein the inflatable device is affixed to the foot support body.

17. The splint of claim 13, further comprising a pump configured to cause air to flow into the inflatable device to inflate the inflatable device.

18. The splint of claim 13, wherein the angle in the second position is 2 degrees or more degrees less than the angle in the first position.

* * * * *